(12) United States Patent
Frölich et al.

(10) Patent No.: US 12,023,223 B2
(45) Date of Patent: Jul. 2, 2024

(54) PATIENT SPECIFIC ADJUSTMENT OF COCHLEAR IMPLANT INSERTION TRAJECTORIES

(71) Applicant: MED-EL Elektromedizinische Geraete GmbH, Innsbruck (AT)

(72) Inventors: Max Frölich, Hannover (DE); Daniel Schurzig, Hannover (DE); Uwe Steinhardt, Hirrlingen (DE)

(73) Assignee: MED-EL ELEKTROMEDIZINISCHE GERAETE GMBH, Innsbruck (AT)

( * ) Notice: Subject to any disclaimer, the term of this patent is extended or adjusted under 35 U.S.C. 154(b) by 789 days.

(21) Appl. No.: 17/043,939

(22) PCT Filed: Apr. 22, 2019

(86) PCT No.: PCT/US2019/028467
§ 371 (c)(1),
(2) Date: Sep. 30, 2020

(87) PCT Pub. No.: WO2019/209690
PCT Pub. Date: Oct. 31, 2019

(65) Prior Publication Data
US 2021/0015674 A1    Jan. 21, 2021

Related U.S. Application Data

(60) Provisional application No. 62/661,203, filed on Apr. 23, 2018.

(51) Int. Cl.
*A61F 11/20*   (2022.01)
*A61N 1/05*    (2006.01)
*A61N 1/36*    (2006.01)

(52) U.S. Cl.
CPC ............ *A61F 11/20* (2022.01); *A61N 1/0541* (2013.01); *A61N 1/36038* (2017.08); *A61F 2210/0014* (2013.01)

(58) Field of Classification Search
CPC .......................... A61N 1/0541; A61N 1/36038
See application file for complete search history.

(56) References Cited

U.S. PATENT DOCUMENTS

| 5,545,219 A | 8/1996 | Kuzma |
| 6,078,841 A | 6/2000 | Kuzma |

(Continued)

FOREIGN PATENT DOCUMENTS

| WO | WO 2007/006574 | 1/2007 |
| WO | WO 2017/182682 | 10/2017 |

OTHER PUBLICATIONS

European Patent Office, Extended European Search Report, Application No. 19792187.7, dated Feb. 23, 2022, 7 pages.

(Continued)

*Primary Examiner* — Christopher A Flory
(74) *Attorney, Agent, or Firm* — BURNS & LEVINSON LLP (57) ABSTRACT

An electrode guide device is described for inserting a cochlear implant electrode array into a scala tympany of a patient cochlea has an electrode guide tube and an end positioner at least partially contained within a cavity of the guide tube at the distal end and slidable within the cavity for adjustable extension beyond the distal end. The end positioner has a natural curvature that is constrained by the cavity of the guide tube for any portion contained within the cavity of the guide tube, and any portion of the end positioner extended beyond the distal end follows the natural curvature. The electrode array can be introduced through the groove of the guide tube along a first directional line towards an electrode opening in the patient cochlea, and then the (Continued)

distal end of electrode array emerging from the guide tube is redirected by the extension of the end positioner along a different second directional line through the electrode opening.

15 Claims, 8 Drawing Sheets

(56) References Cited

U.S. PATENT DOCUMENTS

| | | |
|---|---|---|
| 7,050,858 B1 | 5/2006 | Kuzma et al. |
| 9,474,546 B1 | 10/2016 | Orinski et al. |
| 2010/0094311 A1 | 4/2010 | Jolly et al. |

OTHER PUBLICATIONS

International Searching Authority/US, International Search Report and Written Opinion of the International Searching Authority, Application No. PCT/US2019/028467, dated Aug. 22, 2019, 16 pags.

PATIENT SPECIFIC ADJUSTMENT OF COCHLEAR IMPLANT INSERTION TRAJECTORIES

This application claims priority from U.S. Provisional Patent Application 62/661,203, filed Apr. 23, 2018, which is incorporated herein by reference in its entirety.

FIELD OF THE INVENTION

The present invention relates to an insertion device for cochlear implant electrodes.

BACKGROUND ART

Figure 1:
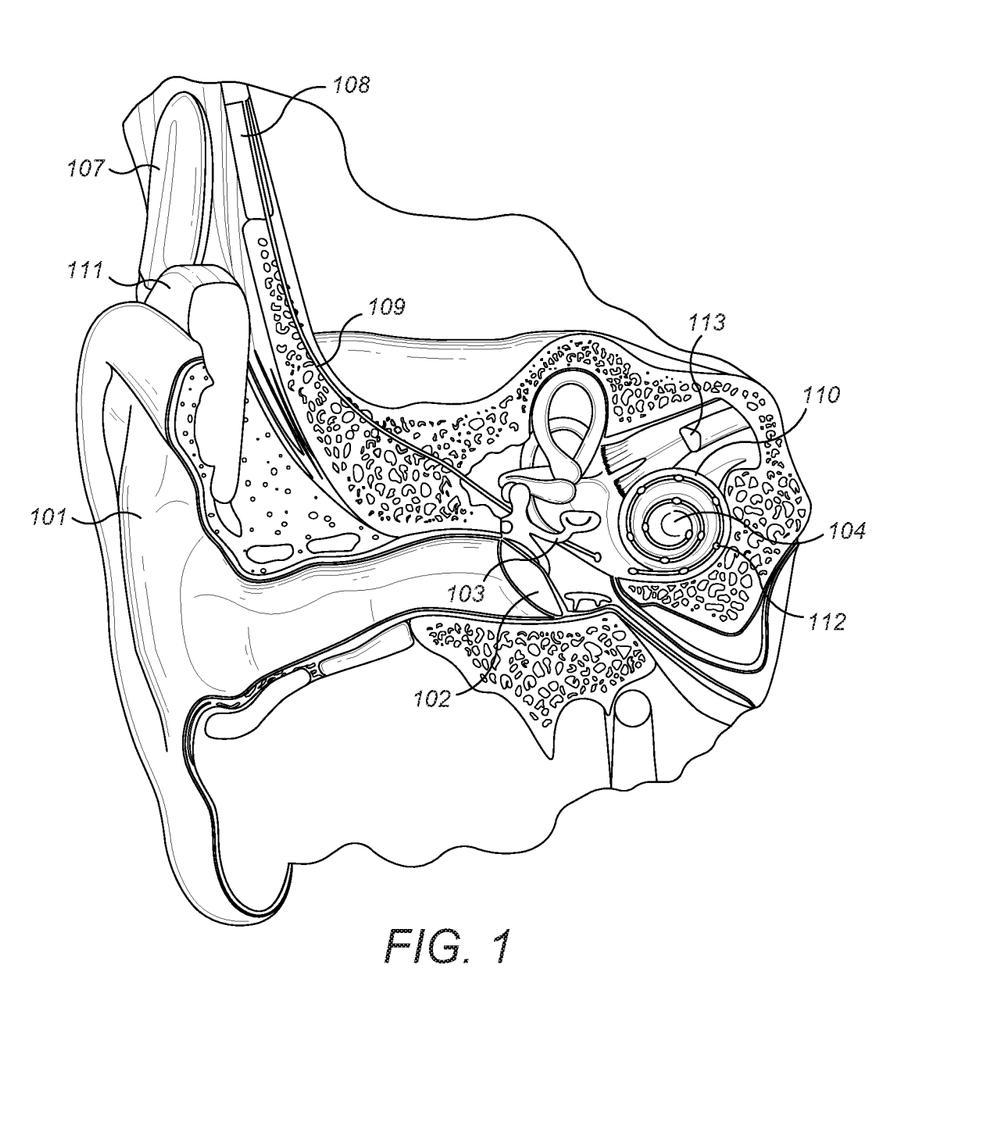
FIG. 1 shows the anatomy of the human ear with a cochlear implant system.

A normal ear transmits sounds as shown in FIG. 1 through the outer ear 101 to the tympanic membrane 102 which moves the bones of the middle ear 103 that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolus where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted electrode can electrically stimulate auditory nerve tissue with small currents delivered by multiple electrode contacts distributed along the electrode.

FIG. 1 also shows some components of a typical cochlear implant system where an external microphone provides an audio signal input to an external signal processor 111 in which various signal processing schemes can be implemented. The processed signal is then converted into a digital data format for transmission by external transmitter coil 107 into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple stimulation contacts 112 on its surface that provide selective stimulation of the cochlea 104.

Figure 2A:
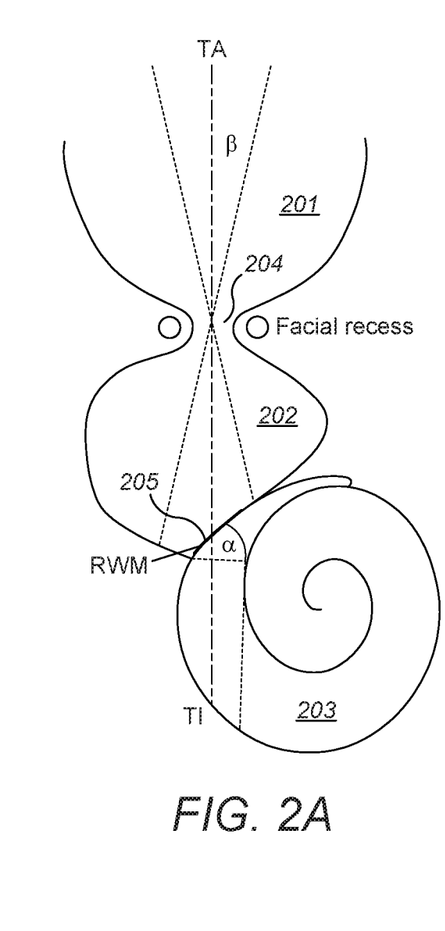
FIGS. 2A-2D show details of electrode insertion geometries in various anatomical circumstances.
Figure 2B:
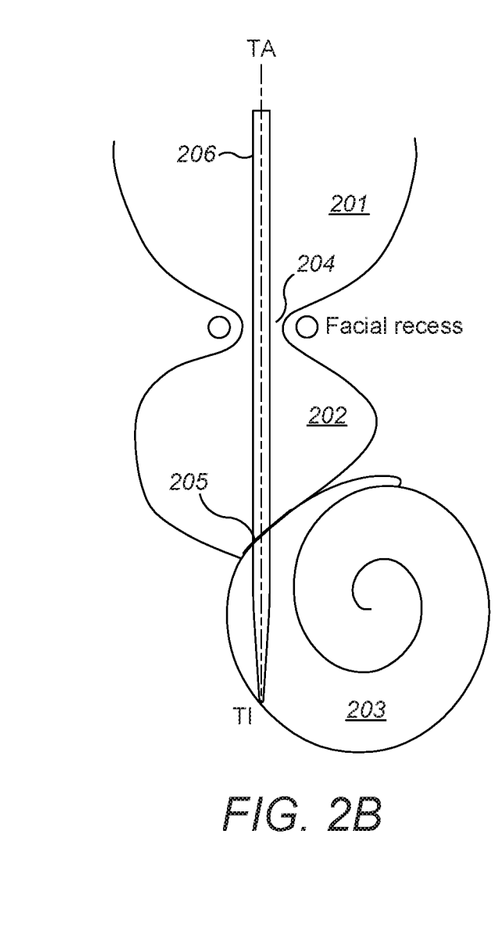

One of the important steps in cochlear implant surgery is the insertion of the electrode array into the scala tympany of the cochlea. Typically this is performed via the round window membrane. As shown in FIGS. 2A-2B, to reach the round window membrane 205, the surgical approach is to drill a posterior tympanotomy 204 at the facial recess of the mastoid bone behind the ear forming cavity 201 (Mastoidectomy), to thereby access the middle ear cavity 202 and the outer surface of the cochlea 203. Other known surgical approaches to reach the round window, can be alternatively used without departing from the inventive concept. The electrode array 206 is then inserted into the scala tympany of the cochlea 203 along that path along a first directional line in a straight access trajectory TA from the facial recess 204 to the round window membrane 205.

The range of possible cochlear access trajectories TA is characterized by the angle β in FIG. 2A and is mostly defined by the size of the posterior tympanotomy 204 itself. On the other hand, the optimal insertion trajectory TI into the cochlea 203, shown in FIG. 2B, is defined by the round window membrane-angle α shown in FIG. 2A. The literature describes a great variance of these angles between individuals (see Breinbauer and Praetorius, *Variability of an Ideal Insertion Vector for Cochlear Implantation*, Otol. Neurotol. January 2015; Avci et al., *Three-Dimensional Force Profile During Cochlear Implantation Depends on Individual Geometry and Insertion Trauma*, Ear and Hearing, December 2016, both of which are incorporated herein by reference in their entireties). This variability can lead to problems in manual insertions of CI electrode arrays. FIGS. 2A-2B demonstrate how manual insertions of CI electrode arrays are feasible if the optimal insertion trajectory TI falls into the range of possible cochlear access trajectories TA. However, due to the anatomical variance in between patients, the two trajectories TA and TI do not always coincide. (The need to redirect the tip of the array prior to RWM insertion has already been recognized by ENT surgeons, and the surgeon sometimes redirects the tip with a simple surgical tool (e.g. suction, needle, fork)).

Figure 2C:
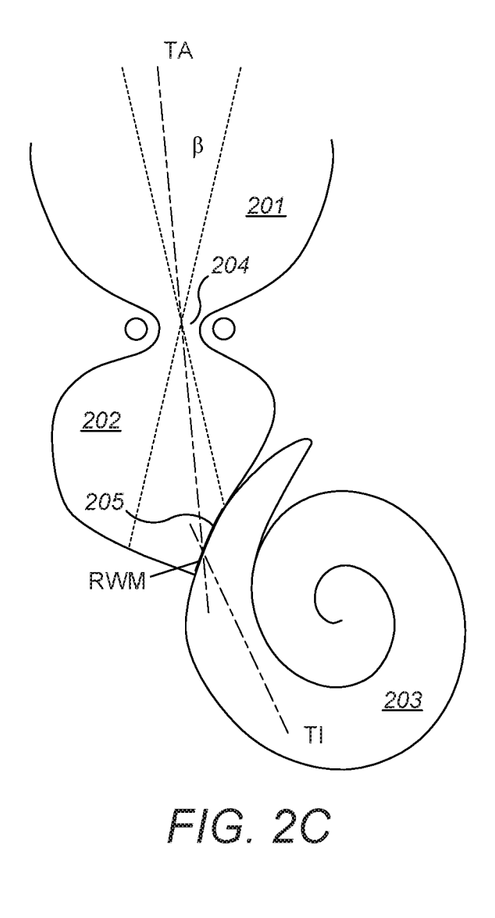
Figure 2D:
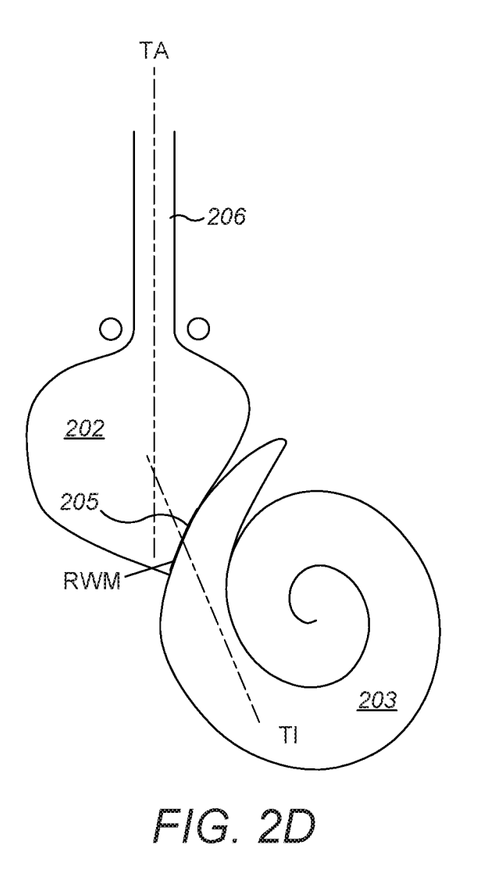

FIGS. 2C-2D shows depictions of two cases in which the limited range of access trajectories TA may lead to difficulties/complications in manual CI insertions. FIG. 2C shows a standard surgical access in which TA and TI do not coincide, which will result in increased contact between the CI electrode array and the cochlear walls, and hence could damage the delicate neural structures within the cochlea 203, and reduce the postoperative residual hearing. FIG. 2D shows an example of a minimally invasive robotic surgical (MIRS) approach, in which a single narrow bore hole 206 from the surface of the skull through the facial recess to the RWM is drilled such that the angle β is basically 0. Therefore, if the bore hole 206 is not planned or cannot be planned for anatomical reasons accurately, insertion of the CI electrode array could become impossible, or else require an additional opening of the tympanic cavity through the tympanic membrane.

Breinbauer and Praetorius discuss optimizing the access trajectory TA through the facial recess, the real opportunities for such optimization actually are quite limited because one still has to work within the boundaries of the access angle β (see FIG. 2C). Thus their approach cannot provide as much flexibility nor as much additional patient safety as is needed.

SUMMARY OF THE INVENTION

Embodiments of the present invention are directed to an intrasurgical electrode guide device for inserting a cochlear implant electrode array into a scala tympany of a patient cochlea. An electrode guide tube has a cavity, a proximal end and a distal end that are connected by a partially enclosed groove with a slot opening along one side to allow loading and/or unloading of a cochlear implant electrode array into the guide tube so that the electrode array can slide within the groove to project a distal end of the electrode array beyond the distal end of the guide tube. An end positioner is at least partially contained within the cavity of the guide tube at the distal end and slidable within the cavity for adjustable extension beyond the distal end. The end positioner is characterized by a natural curvature that is constrained by the guide tube for any portion contained within the cavity of the guide tube, and any portion of the end positioner extended beyond the distal end follows the natural curvature. The guide tube and the end positioner are configured for controlled cooperation by a surgeon so that the electrode array can be introduced through the groove of the guide tube along a first directional line towards an electrode opening in an outer surface of the patient cochlea, and then the distal end of electrode array emerging from the guide tube at the distal end is redirected by the extension of the end positioner along a different second directional line through the electrode opening into the scala tympany.

In further specific embodiments, the guide tube may be configured to fit through a posterior tympanotomy in the facial recess along the first directional line towards the electrode opening. The guide tube may be configured to have an adjustable length. The end positioner may be made of a material with spring properties or a shape memory alloy or other suitable materials with resilient properties. And the electrode guide device may further include an electrode pushing mechanism configured to slide the electrode array within the groove to project the distal end of the electrode array out along the end positioner towards the electrode opening.

Embodiments of the present invention also include a related method for inserting a cochlear implant electrode array into a scala tympany of a patient cochlea. A surgical opening is created through skin and skull bone of a recipient patient into the middle ear cavity. An electrode guide device is inserted through the surgical opening into the middle ear cavity towards an electrode opening location on an outer surface of a patient cochlea, wherein the electrode guide device has: (i) an electrode guide tube with a cavity, a proximal end and a distal end connected by a partially enclosed groove having a slot opening along one side to allow loading and/or unloading of a cochlear implant electrode array into the guide tube so that the electrode array can slide within the guide tube to project a distal end of the electrode array beyond the distal end of the guide tube, and (ii) an end positioner that is at least partially contained within the cavity of the guide tube at the distal end, and slidable within the cavity for adjustable extension beyond the distal end, wherein the end positioner is characterized by a natural curvature that is constrained by the guide tube for any portion of the end positioner contained within the guide tube, and wherein any portion of the end positioner extended beyond the distal end follows the natural curvature. An endoscope is then pushed through the guide tube to the distal end so as to enable visual observation by a surgeon through the endoscope of the outer surface of the patient cochlea. The guide tube and the end positioner are operated to extend the endoscope and a portion of the end positioner beyond the distal end along its natural curvature until visual observation through the endoscope indicates that the end positioner is pointing along a directional line towards the electrode opening location at an optimal electrode array insertion angle. The endoscope is withdrawn from the guide tube. The cochlear implant electrode array is loaded through the proximal end into the guide tube, and then the cochlear implant electrode array slides through the groove of the guide tube to project a distal end of the electrode array beyond the distal end of the guide tube and the extended portion of the end positioner, through the electrode opening and into the scala tympany of the cochlea along the directional line.

Further specific such embodiments may also include forming the electrode opening at the electrode opening location, either before pushing the endoscope through the guide tube or after withdrawing the endoscope from the guide tube. The surgical opening may specifically be a posterior tympanotomy in a facial recess of the skull bone. The guide tube may be configured to have an adjustable length. The end positioner may be made of a material with spring properties or a shape memory alloy or other suitable materials with resilient properties. And the electrode device may further include an electrode pushing mechanism configured to slide the electrode array within the groove of the guide tube to project the distal end of the electrode array out along the end positioner towards the electrode opening.

DETAILED DESCRIPTION OF SPECIFIC EMBODIMENTS

Embodiments of the present invention are directed to an intrasurgical electrode guide device for inserting a cochlear implant electrode array into a scala tympany of a patient cochlea. The inventive arrangement as described more fully below represents a new approach for connecting the access trajectory TA and the insertion trajectory TI in a patient specific manner. In contrast to earlier proposals (e.g. Breinbauer and Praetorius) this does not align TA and TI within the possibilities given by anatomical boundary conditions, but instead redirects the electrode array from TA onto TI prior to RWM insertion. This adds additional degrees of freedom to the insertion procedure for a more flexible and less restrained insertion of the electrode array. This additional flexibility is especially important if the RWM is difficult to access. The tool itself comprises two components: an electrode guide device that is inserted through the posterior tympanotomy toward the round window membrane, and an end positioner that extends from the distal end to allow directing the tip of an enclosed electrode array at the RWM at an optimal angle for the specific geometry of the patient being implanted.

Figure 3A:
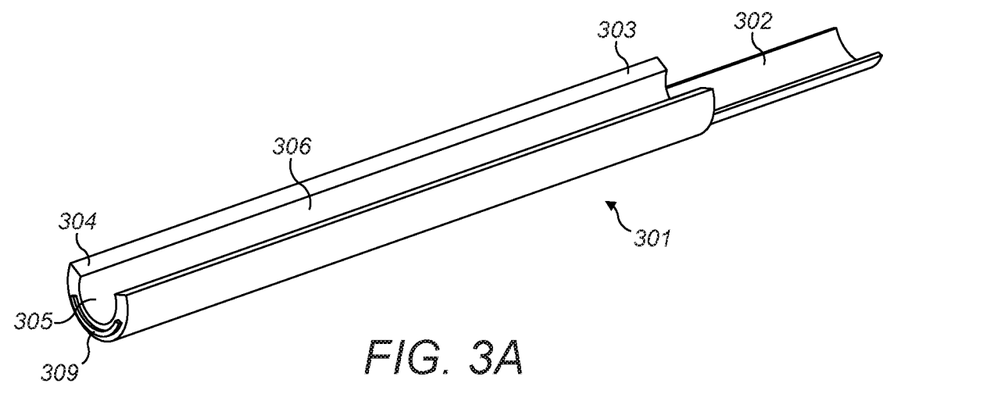
FIGS. 3A-3C show structural details of an electrode insertion device according to an embodiment of the present invention.
Figure 3B:
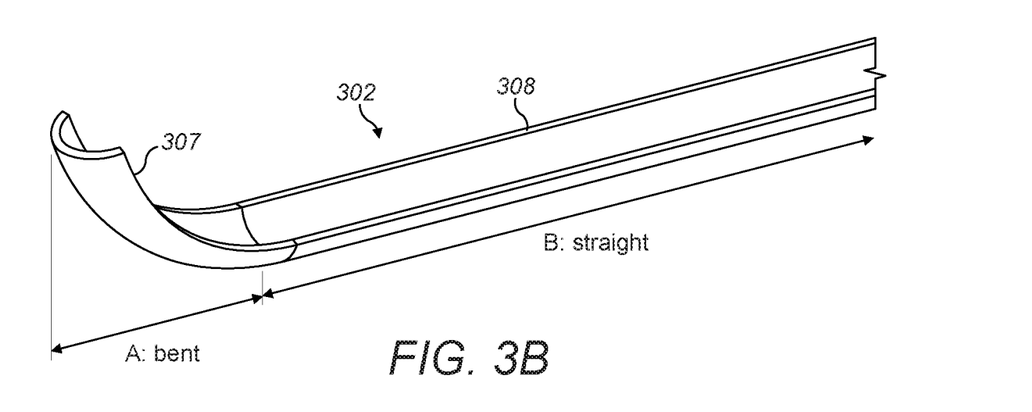
Figure 3C:
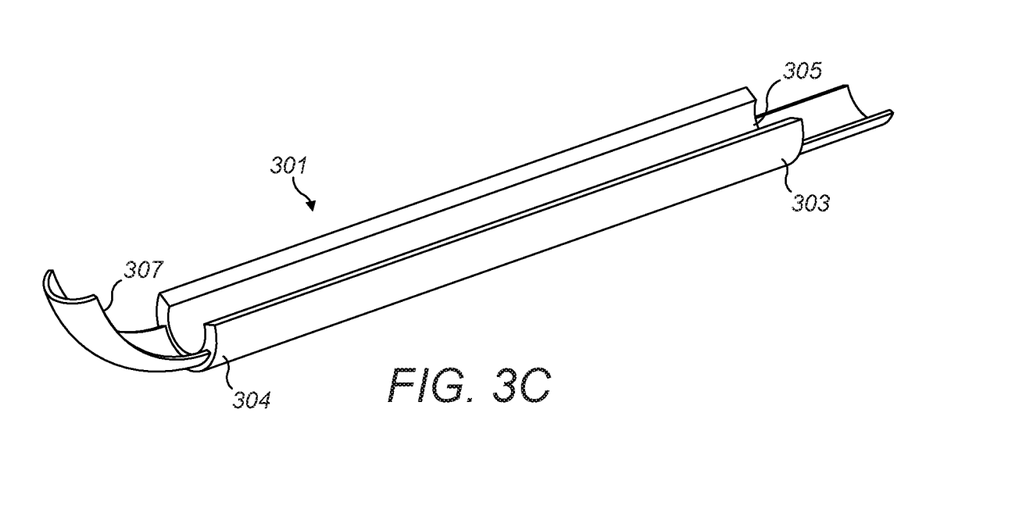

FIGS. 3A-3C show structural details of an electrode insertion device according to an embodiment of the present invention. An electrode guide tube 301 has a proximal end 303 and a distal end 304 that are connected by a partially enclosed groove 305 with a slot opening 306 along one side to allow loading and/or unloading of a cochlear implant electrode array into the guide tube 301 so that the electrode array can slide within groove 305 of the guide tube 301 to project a distal end of the electrode array beyond the distal end 304 of the guide tube 301. The guide tube 301 may be configured to have an adjustable length.

The guide tube 301 also contains a cavity 309 which contains and restrains an end positioner 302 that is at least partially contained within the guide tube 301 at the distal end 304 and slidable within cavity 309 for adjustable extension beyond the distal end 304. The end positioner 302 is characterized by a straight section 308 and a curved section 307 that is constrained by the guide tube 301 for any portion contained within the cavity 309 of the guide tube 301. Any portion of the curved section 307 that is extended beyond the distal end 304 of the guide tube 301 follows its natural curvature. The electrode guide device may further include an electrode pushing mechanism (not shown) that is configured to slide the electrode array within the groove 305 to project the distal end of the electrode array out along the end positioner 302 towards the electrode opening.

The end positioner 302 may be made of a thermoplastic material or a shape memory alloy or any other material having spring properties and in addition may be further able to sustain high strain without damage. The cross sectional geometry of the end positioner 302 corresponds to the geometry of cavity 309 inside the guide tube 301 that contains it, such that the end positioner 302 can be fed through the cavity from the proximal end 303 of the guide tube 301. When the naturally curved section 307 is contained within the cavity of the guide tube 301 and straightened out, it experiences elastic loading leading to the generation of strain. When the curved section 307 of the end positioner 302 is extended from the cavity beyond the distal end 304, the corresponding geometrical boundaries of the containing cavity are removed and the strain in the curved section 307 recovers and bends back to its natural shape. The further the end positioner 302 is extended, the larger is the unrestrained portion of the curved section 307 which is no longer restrained, and the greater the curvature/redirection. Thus, the axial movement of the end positioner 302 with respect to the guide tube 301 defines the degree of redirection.

The guide tube 301 and the end positioner 302 are configured for controlled cooperation by a surgeon so that the electrode array can be introduced through groove 305 of the guide tube 301 along a first directional line (i.e., access trajectory TA) towards the electrode opening location 406. Then the distal end of electrode array emerging from the guide tube 301 at the distal end 304 is redirected by the extension of the end positioner 302 along a different second directional line (i.e., insertion trajectory TI) through the electrode opening into the scala tympany. If the end positioner 302 is entirely contained within the guide tube 301 and not at all deployed beyond the distal end 304, then a device fed through the groove 305 inside the guide tube 301 (e.g., an endoscope or the electrode array) then will exit the distal end 304 in a straight direction along the first directional line (TA). As the curved portion 307 of the end positioner 302 is extended beyond the distal end 304 of the guide tube 301, then the exit trajectory (second directional line) of devices fed through the groove 305 inside the guide tube 301 depends on how far the end positioner 302 is deployed and the specific pre-bent shape of the curved portion 301.

Figure 4A:
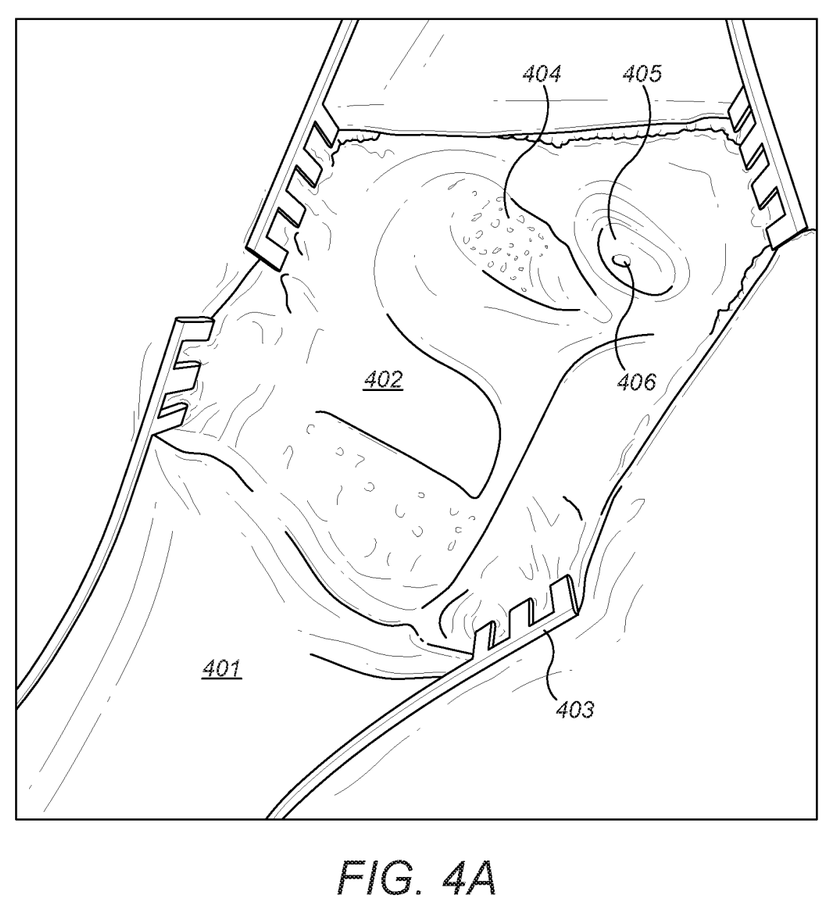
FIGS. 4A-4B show details of implantation surgery using a device according to an embodiment of the present invention.
Figure 4B:
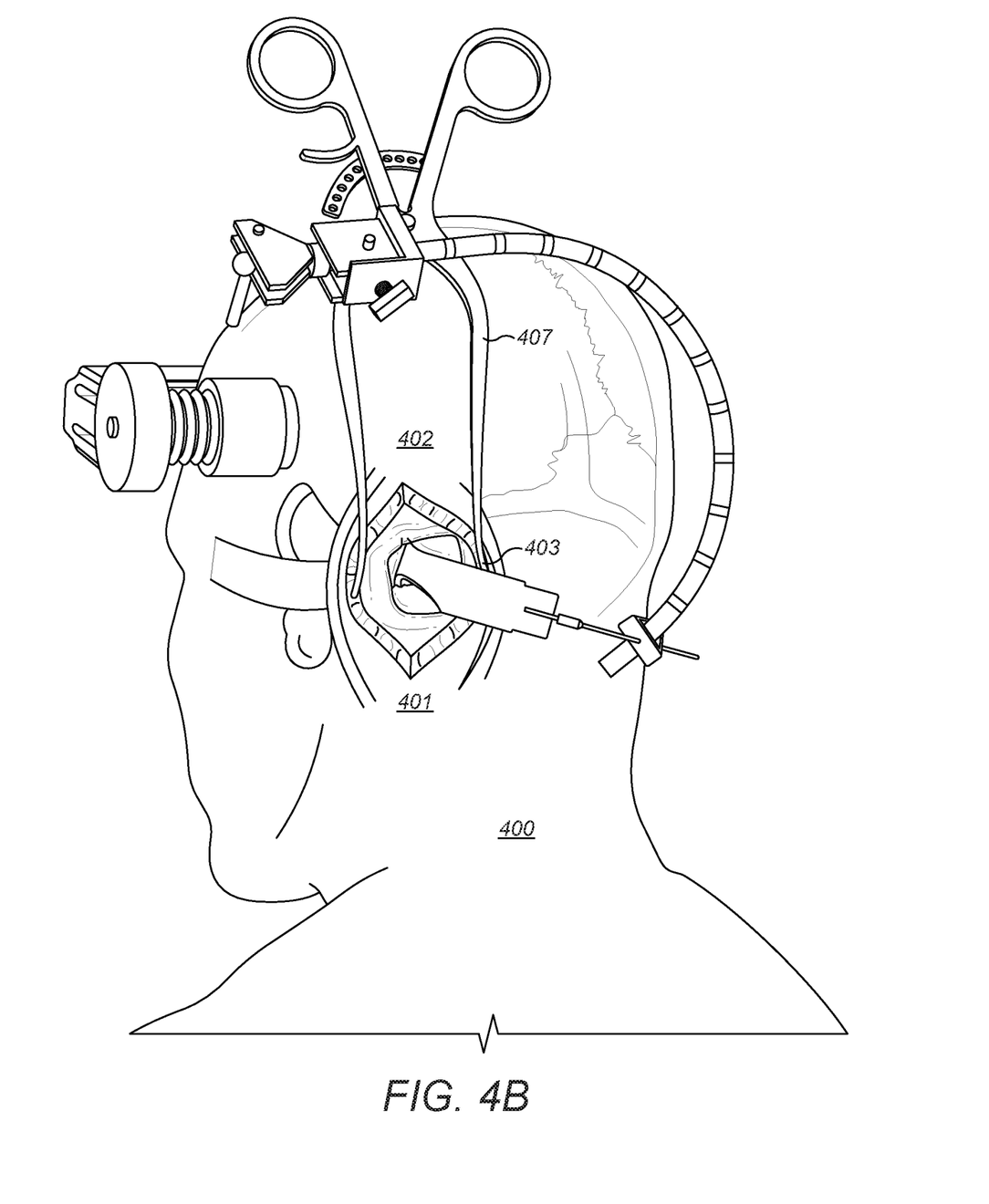

Using this kind of tool, cochlear implantation following optimized insertion trajectories can be performed. As shown in FIGS. 4A-4, a surgical opening 404 is created through skin 401 and skull bone 402 of a recipient patient into the middle ear cavity. For example, the surgical opening 404 may typically be a posterior tympanotomy in the facial recess of the mastoid bone. An electrode guide device can then be mounted onto a surgical retractor 407 (e.g. Apfelbau-Retractor) that is fixed in the surgical opening 404. The electrode guide device can then be inserted through the surgical opening 404 into the middle ear cavity towards an electrode opening location 406 on an outer surface 405 of a patient cochlea.

Figure 5A:
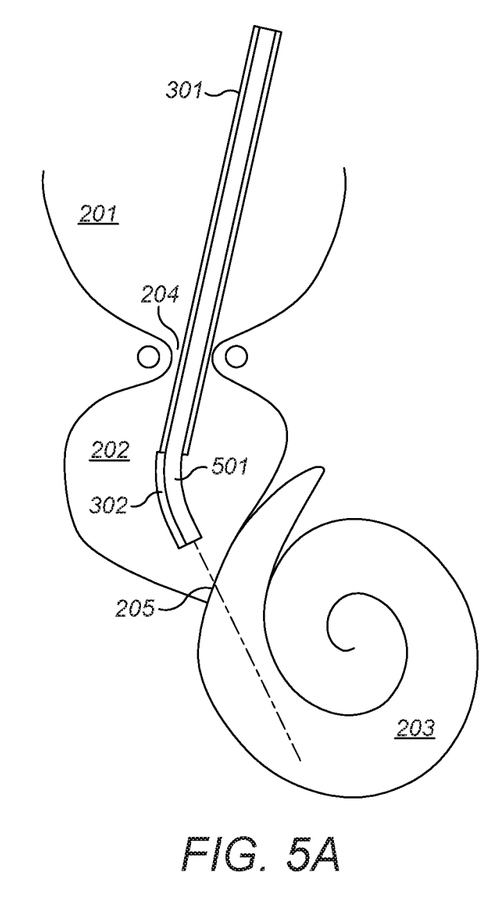
FIGS. 5A-5B show further details of implantation surgery according to an embodiment of the present invention.

As shown in FIG. 5A, an endoscope 501 can then be pushed through the guide tube 301 to the distal end so as to enable visual observation by a surgeon through the endoscope 501 of the round window membrane 205 on the outer surface of the patient cochlea tool to assess the anatomical boundary conditions of the individual patient. The guide tube 301 and the end positioner 302 are operated to extend a portion of the end positioner 302 and the endoscope 501 beyond the distal end of the guide tube 301 until visual observation through the endoscope 501 indicates that the end positioner 302 is pointing along a directional line towards the round window membrane 205 at an optimal electrode array insertion angle following the optimal insertion trajectory TI.

Figure 5B:
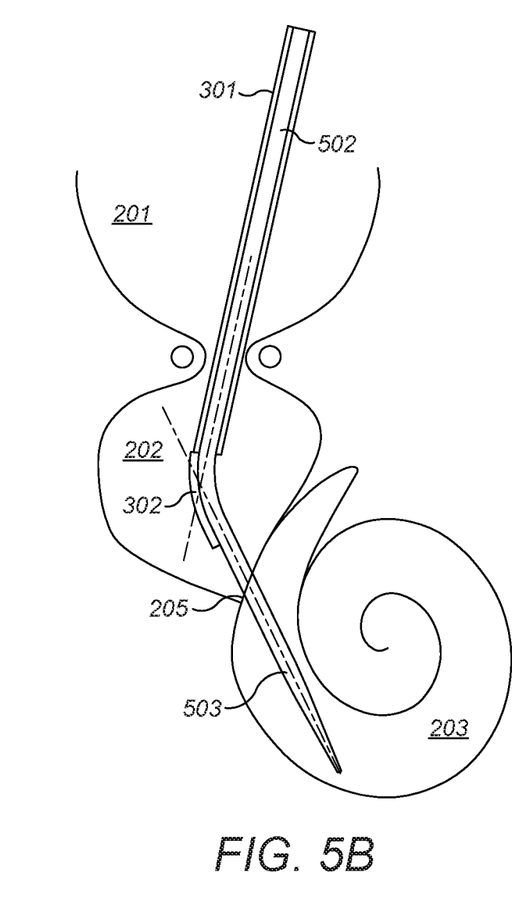

Once the trajectory is correctly set, the guide tube 301 and the end positioner 302 are held in place, and the endoscope 501 is withdrawn through groove 305 from the guide tube 301. As shown in FIG. 5B, the cochlear implant electrode array 503 is loaded through the proximal end 303 into groove 305 of the guide tube 301. The electrode array 503 slides through groove 305 of the guide tube 301 to project a distal end of the electrode array 503 beyond the distal end of the guide tube 301 and the extended portion of the end positioner 302, through the electrode opening in the round window membrane 205 and into the scala tympany of the cochlea following the previously defined trajectory TI. In specific embodiments, the actual electrode opening in the round membrane 205 can be created either before pushing the endoscope 501 through the guide tube 301, or after withdrawing the endoscope 501 from the guide tube 301. After successful electrode array 503 insertion, the end positioner 302 must be retracted such that its distal end is entirely contained within cavity 309 of the guide tube 301. Subsequently, guide tube 301 and the therein contained end positioner 302 can then be retracted from the surgical site with the electrode lead sliding through groove 305 and slot opening 306 of guide tube 301.

Figure 6A:
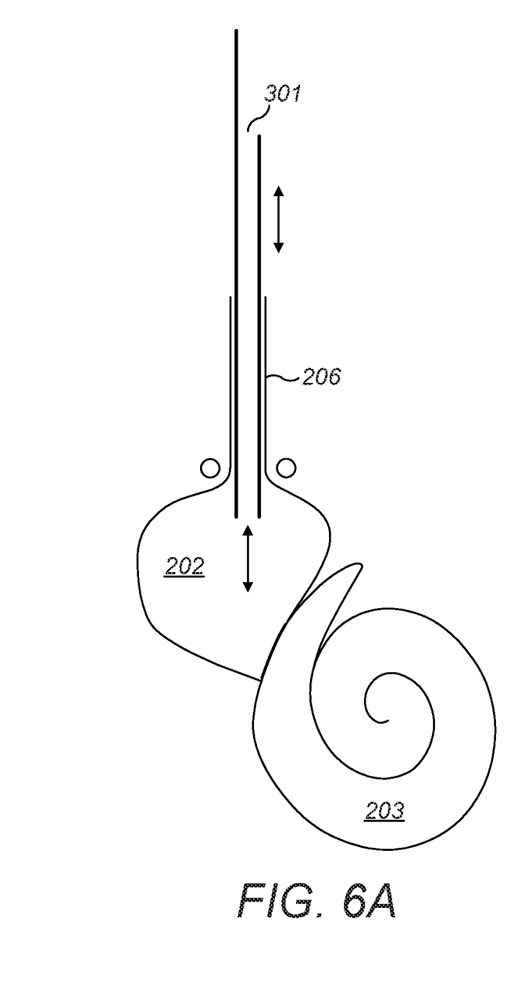
FIGS. 6A-6C illustrate the various degrees of freedom of movement provided by embodiments of the present invention.
Figure 6B:
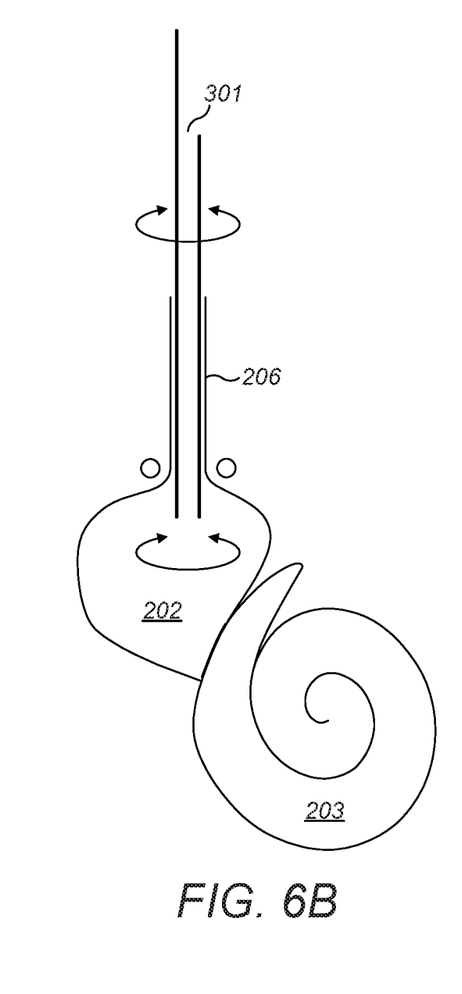
Figure 6C:
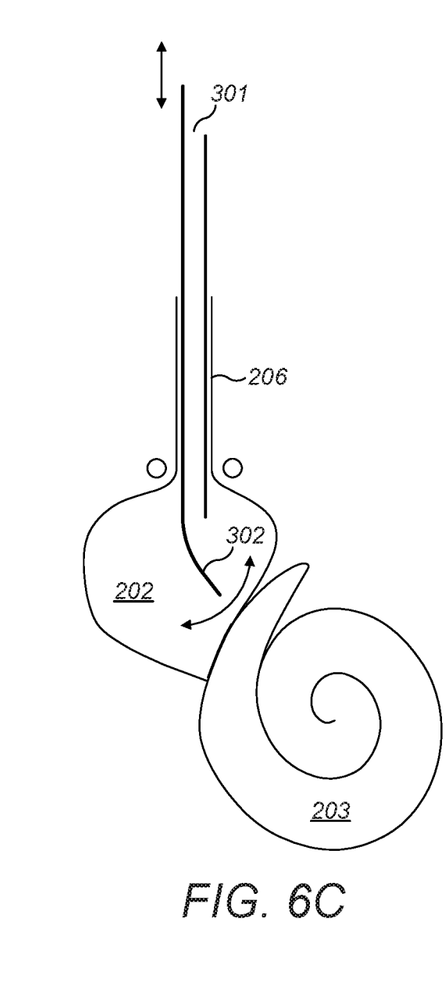

In the case of an MIRS approach where only a single drill hole is generated from the surface of the skull to the opening of the cochlea, the use of the described electrode insertion device becomes especially significant because it generates three degrees of freedom with respect to the insertion trajectory TI. As shown in FIGS. 6A-6C, these degrees of freedom can be manipulated by translation (FIG. 6A) and rotation (FIG. 6B) of the guide tube, as well as extension and retraction of the end positioner relative to the guide tube (FIG. 6C).

Insertion of the electrode array into the scala tympany becomes adjustable to the angle of the RWM and is no longer limited by the access of the posterior tympanotomy. This provides more freedom in planning the access trajectory TA with a stronger focus onto patient safety since the insertion trajectory TI can be adjusted afterwards. Furthermore, in minimally invasive or MIRS surgery, the electrode guide device enables alternative access routes to the RWM (i.e. transtympanal, supraincudial, etc.) when the trajectory of drilling is decoupled from the trajectory of insertion.

Although various exemplary embodiments of the invention have been disclosed, it should be apparent to those skilled in the art that various changes and modifications can be made which will achieve some of the advantages of the invention without departing from the true scope of the invention.

What is claimed is:

1. An intrasurgical electrode guide device for inserting an electrode array of a cochlear implant into a scala tympany of a patient cochlea, the device comprising:
   a guide tube having a cavity, a proximal end and a distal end connected by a partially enclosed groove having a slot opening along one side to allow loading and/or unloading of the electrode array into the guide tube so that the electrode array can slide within the groove to project a distal end of the electrode array beyond the distal end of the guide tube; and
   an end positioner having a straight section at its proximal end and a curved section at its distal end, the end positioner slidable and retractable within the cavity and configured so that the curved section is entirely contained within the cavity in a retracted position and the curved section extends beyond the distal end of the guide tube in an extended position,
   wherein the guide tube and the end positioner are configured for controlled cooperation by a surgeon so that the electrode array can be introduced through the groove of the guide tube along a first directional line towards an electrode opening in an outer surface of the patient cochlea, and then the distal end of the electrode array emerging from the distal end of the guide tube is redirected by the curved section of the end positioner in the extended position along a different second directional line through the electrode opening into the scala tympany.

2. The electrode guide device according to claim 1, wherein the guide tube is configured to fit through a posterior tympanotomy in the facial recess along the first directional line towards the electrode opening.

3. The electrode guide device according to claim 1, wherein the guide tube is configured to have an adjustable length.

4. The electrode guide device according to claim 1, wherein the end positioner is made of a material with spring properties.

5. The electrode guide device according to claim 1, wherein the end positioner is made of a shape memory alloy.

6. The electrode guide device according to claim 1, further comprising:
   an electrode pushing mechanism configured to slide the electrode array within the groove to project the distal end of the electrode array out along the end positioner towards the electrode opening.

7. A method for inserting an electrode array of a cochlear implant into a scala tympany of a patient cochlea, the method comprising:
   creating a surgical opening through skin and skull bone of a recipient patient into the middle ear cavity;
   inserting an electrode guide device through the surgical opening into the middle ear cavity towards an electrode opening location on an outer surface of a patient cochlea, wherein the electrode guide device comprises:
   i. a guide tube having a cavity, a proximal end and a distal end connected by a partially enclosed groove having a slot opening along one side to allow loading and/or unloading of the electrode array into the guide tube so that the electrode array can slide within the groove of the guide tube to project a distal end of the electrode array beyond the distal end of the guide tube, and
   ii. an end positioner having a straight section at its proximal end and a curved section at its distal end, the end positioner slidable within the cavity and configured so that the curved section is entirely contained within the cavity in a retracted position and the curved section extends beyond the distal end of the guide tube in an extended position;
   pushing an endoscope through the guide tube to the distal end so as to enable visual observation by a surgeon through the endoscope of the outer surface of the patient cochlea;
   operating the guide tube and the end positioner to extend the endoscope and the curved section of the end positioner beyond the distal end of the guide tube in the extended position until visual observation through the endoscope indicates that the curved section of the end positioner is pointing along a directional line towards the electrode opening location at an optimal electrode array insertion angle;
   withdrawing the endoscope from the guide tube;
   loading the electrode array through the proximal end of the guide tube; and
   sliding the electrode array through the groove of the guide tube to project a distal end of the electrode array beyond the distal end of the guide tube and the curved section of the end positioner in the extended position, through the electrode opening and into the scala tympany of the cochlea along the directional line.

8. The method according to claim 7, further comprising:
   forming the electrode opening at the electrode opening location.

9. The method according to claim 8, wherein the electrode opening is formed before pushing the endoscope through the guide tube.

10. The method according to claim 8, wherein the electrode opening is formed after withdrawing the endoscope from the guide tube.

11. The method according to claim 7, wherein the surgical opening is a posterior tympanotomy in a facial recess of the skull bone.

12. The method according to claim 7, wherein the guide tube is configured to have an adjustable length.

13. The method according to claim 7, wherein the end positioner is made of a material with spring properties.

14. The method according to claim 7, wherein the end positioner is made of a shape memory alloy.

15. The method according to claim 7, wherein the electrode device further includes an electrode pushing mechanism configured to slide the electrode array within the groove to project the distal end of the electrode array out along the end positioner towards the electrode opening.

* * * * *